(12) United States Patent
McKinley (10) Patent No.: US 7,226,413 B2
(45) Date of Patent: Jun. 5, 2007

(54) NERVE ROOT RETRACTOR AND SUCKER

(75) Inventor: Laurence M. McKinley, Escondido, CA (US)

(73) Assignee: Aeolin LLC, Escondido, CA (US)

( * ) Notice: Subject to any disclaimer, the term of this patent is extended or adjusted under 35 U.S.C. 154(b) by 631 days.

(21) Appl. No.: 10/715,684

(22) Filed: Nov. 17, 2003

(65) Prior Publication Data
US 2005/0107671 A1 May 19, 2005

(51) Int. Cl.
*A61B 1/32* (2006.01)
(52) U.S. Cl. ............................ 600/210; 604/902
(58) Field of Classification Search ............ 433/95, 433/96; 604/30, 902, 35, 540, 541; 600/206, 600/210
See application file for complete search history.

(56) References Cited

U.S. PATENT DOCUMENTS

| 1,621,212 | A | | 3/1927 | Myers |
| 3,516,160 | A | * | 6/1970 | Leffler ........................ 433/95 |
| 4,049,000 | A | | 9/1977 | Williams |
| 4,715,071 | A | | 12/1987 | Henkin et al. |
| 4,992,047 | A | * | 2/1991 | Warner ........................ 433/91 |
| 5,123,403 | A | | 6/1992 | Lavyne |
| 5,358,507 | A | * | 10/1994 | Daily ......................... 606/159 |
| 5,743,736 | A | * | 4/1998 | Folko et al. .................. 433/96 |
| 5,902,315 | A | | 5/1999 | DuBois |
| 5,961,522 | A | * | 10/1999 | Mehdizadeh ................. 606/79 |
| 5,971,920 | A | * | 10/1999 | Nagel ......................... 600/206 |
| 6,129,547 | A | * | 10/2000 | Cise et al. .................... 433/80 |
| 6,241,658 | B1 | | 6/2001 | Goodrich |
| 6,248,061 | B1 | | 6/2001 | Cook, Jr. |
| 2004/0143164 | A1 | * | 7/2004 | Suddaby ..................... 600/210 |
| 2004/0143165 | A1 | * | 7/2004 | Alleyne ...................... 600/210 |

* cited by examiner

*Primary Examiner*—Cary E. O'Connor
(74) *Attorney, Agent, or Firm*—Christie, Parker & Hale, LLP (57) ABSTRACT

An ergonomically and functionally improved combination nerve root retractor and sucker device, system, and methods of using such a nerve root retractor and sucker are provided. The nerve root retractor and sucker of the current invention having an adjustable geometry nerve root retractor/sucker shaft.

23 Claims, 6 Drawing Sheets

NERVE ROOT RETRACTOR AND SUCKER

FIELD OF THE INVENTION

The present invention is directed to a nerve root retractor and sucker; and more particularly to a nerve root retractor and sucker having an adjustable geometry.

BACKGROUND OF THE INVENTION

In the field of lumbar disc surgery there are no two more important tools than the nerve root retractor and the sucker. During an operation, the nerve root retractor is used by a medical professional to hold the nerve to one side so that the operating surgeon can remove disc material without damaging the nerve. In turn the sucker is used in turn to remove blood or other fluids that accumulate in the surgical area to ensure that the medical professional has good visualization of the surgical area during operation.

In such spinal surgery, the design of the sucker and nerve root retractor are very important. For example, most lumbar disc surgery suckers have a small vent hole on the top of the device such that exposing the hole leads to an instantaneous reduction in the suction force being applied to the surgical region. The ability to reduce the suction is important because during surgery the dura, or covering material in the spine is periodically breached, spinal fluid leaks out and sometimes washes nerve roots out of the dural sac. These nerve roots can get sucked into the sucker and if no mechanism for instantly reduction the suction were available the possibility would exist that the sucker could suck the nerve out through the rent in the dura and shear and/or traumatize the nerve root, possible damaging it irreparably. The vent in the sucker allows a medical professional to grossly regulate the suction being applied by the nerve sucker thereby reducing the chances of such a catastrophic injury.

Although the nerve root retractor and the sucker have been used in surgery for many years, they require two separate hands of a highly trained medical personnel for proper operation. Having extra personnel during surgery is very costly and many insurance companies are no longer authorizing or paying for assistants for surgeons during these delicate operations. To address this new medical reality some companies have introduced dual purpose tools for both retracting and sucking. One exemplary nerve root retractor and sucker was made by Karlin Technology, Inc (Part # 46-3005). However, these devices were generally clumsy, bulky, and inflexible, and are therefore difficult to use for the delicate procedures required during lumbar disc surgery.

Accordingly, a need exists for an ergonomically and functionally improved nerve root retractor and sucker for use in lumbar disc surgery, if necessary for use by a solo spine surgeon who has no assistant.

SUMMARY OF THE INVENTION

The present invention is directed to an ergonomically and functionally improved combination nerve root retractor/sucker having an adjustable geometry.

In one embodiment, the nerve root retractor and sucker comprises a handle having an adjustable retractor/sucker shaft attached thereto. In one such embodiment the angle of the shaft is polyaxially adjustable with respect to the handle. In another such embodiment the handle may be designed to ergonomically fit within the hand, or may be provided with a non-slip surface, such as a knurled surface, to prevent slippage.

In another embodiment, the retractor/sucker shaft is detachable from the handle such that retractor/sucker shafts of different designs may be interchangeably attached to the handle. In one such embodiment nerve root retractor/sucker shafts having different lengths, such as from 80 to 200 mm; different widths of the retractor portion of the device (such as from 5 to 12 mm; or having different fixed angles with respect to the handle may be interchanged, such as around 135 degrees. Alternatively, the nerve root retractor/sucker shaft may be designed with a low profile or offset bayonet design shaft for use with a microscope.

In yet another embodiment, the nerve root retractor/sucker shaft may be constructed of malleable materials, such as plastics or thin bodied metal tubes such that the shaft can be manually bent to conform to a desired shape, by the operating surgeon at his wish.

In still another embodiment, the handle incorporates a fixing clamp to fix the position of the retraction/suction shaft with respect to the handle when in a desired conformation.

In still yet another embodiment, the handle incorporates a suction control mechanism. In one such embodiment the suction control mechanism comprises at least one vent hole bored into the handle in communication with the suction source. In another such embodiment the handle comprises a multiplicity of vent holes such that variable suction control can be provided.

In still yet another embodiment the invention is directed to a nerve root retractor and sucker system.

In still yet another embodiment the invention is directed to a method of performing a lumbar disc operation using a nerve root retractor and sucker as described herein.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE INVENTION

The present invention is directed to an ergonomically and functionally improved combination nerve root retractor and sucker.

Figure 1A:
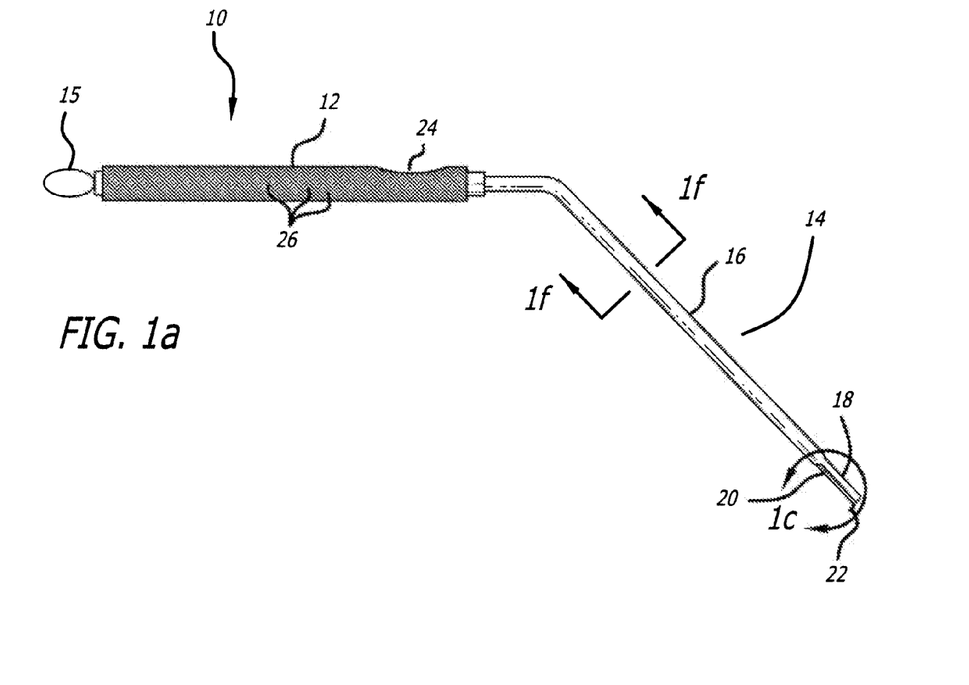
FIG. 1a is a side view of a first embodiment of a nerve root retractor and sucker in accordance with the present invention.

FIGS. 1a to 1f show one embodiment of a nerve root retractor and sucker in accordance with the current invention. As shown in FIG. 1a, the nerve root retractor and sucker 10 of the current invention generally comprises a handle portion 12 having a nerve root retractor/sucker shaft 14 attached at one end thereof and having a suction connection 15 at the opposite end thereof. The nerve root retractor/sucker shaft itself comprises a hollow suction tube 16 for providing suction through a suction opening 18 at the tip 20 of the shaft and a retractor 22 for physically manipulating a nerve during operation.

Figure 1B:
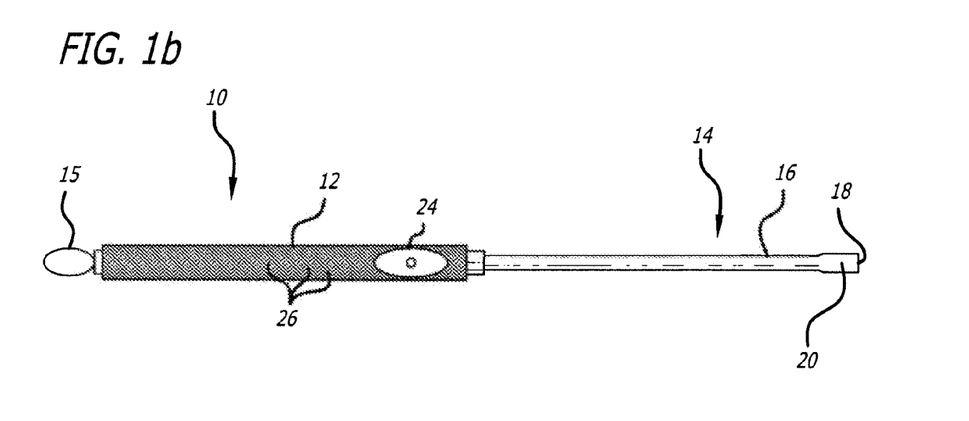
FIG. 1b is a top view of a first embodiment of a nerve root retractor and sucker in accordance with the present invention.

In the embodiment shown in FIGS. 1a and 1b, the handle 12 is hollow such that it may provide a fluid connection between the suction source (not shown) attached at the suction connection 15 and the suction tube 16. A suction control vent 24 is bored into the handle of the apparatus to provide the user a manual means for reducing the suction provided to the tip of the apparatus during operation. Specifically, during operation if the vent is covered by the user then maximum suction is provided at the suction opening, but when the vent is left open the suction is reduced to the extent that air enters the vent into the handle. Although only a single vent 24 is shown in the embodiment picture in FIG. 1b, it should be understood that any number and size of suction vents could be provided such that variable control of the intensity of the suction provided at the tip of the device may be provided.

Although in the embodiment shown in FIG. 1a the shaft 14 forms a 135 degree angle to the axis of the handle 12, it should be understood that any desired angle may be set into the apparatus. Likewise, although specific handle and shaft dimensions are shown in FIGS. 1a and 1b it should be understood that these dimensions may be altered depending on the desired geometry of the apparatus. Preferred dimensions for the device include shaft lengths from about 80 to about 220 mm, while the width of the apparatus, and particularly the retractor, is preferably about 5 to about 12 mm.

In addition, although one handle design having a knurled surface 26 is shown in FIGS. 1a and 1b, it should be understood that any suitable handle design may be utilized with the current invention such that a retractor/sucker shaft may be attached thereto, and suction control provided to the shaft. For example, the handle could be designed with a pistol grip or could be contoured to the hand such that the ergonomic fit of the device is better tailored to the user.

Figure 1C:
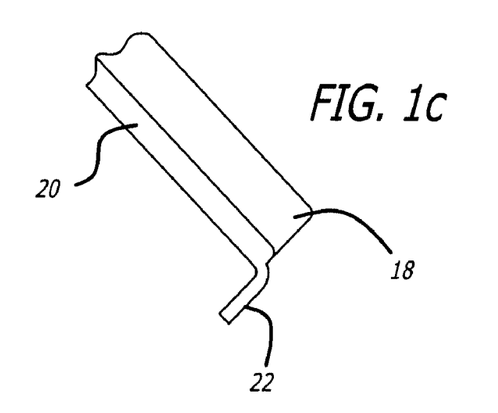
FIG. 1c is a detailed view, "view-A" identified in FIG. 1a, of a first embodiment of a nerve root retractor and sucker in accordance with the present invention.

FIGS. 1a to 1c provide more detail into the design of the shaft 14 and the tip 20 of the shaft. As shown in FIG. 1c, the tube 16 and the retractor 22 are proximately positioned one to the other such that suction may be applied and the nerve retracted simultaneously during operation. As shown in this embodiment, the retractor 22 comprises a flat blade fixedly attached to the tube 16. Although specific dimensions, angles and geometries of retractor blades are shown in this embodiment, it should be understood that any retractor blade suitable for retracting nerves during spinal surgery may be utilized in the current invention. For example, the blade may be differently dimensioned, or angled, such as in a swept back geometry, to provide a desired control geometry to the user. Alternatively, the retractor could be made adjustable, such as by having a retractable and/or variable length blade, and/or by having a pivotable variable angle blade if so desired.

Figure 1D:
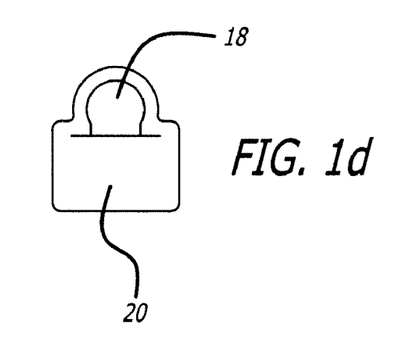
FIG. 1d is a cross-section taken along line "A-A" of FIG. 1a of a first embodiment of a nerve root retractor and sucker in accordance with the present invention.
Figure 1E:
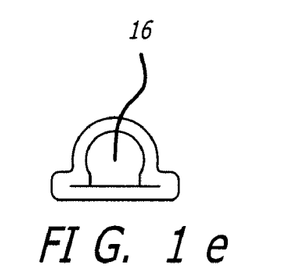
FIG. 1e is a cross-section taken along line "B-B" of FIG. 1a of a first embodiment of a nerve root retractor and sucker in accordance with the present invention.
Figure 1F:
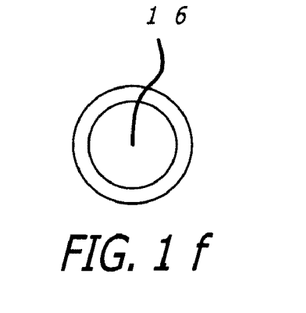
FIG. 1f is a cross-section taken along line "C-C" of FIG. 1a of a first embodiment of a nerve root retractor and sucker in accordance with the present invention.

As shown in FIGS. 1d to 1f, in this embodiment because of the retractor/suction combination, the cross-section of the tube 16 changes along the length of the shaft 14 from a semi-circular geometry at the tip 20 to a full circular geometry as it approaches the handle 12. Although one particular tube design is shown herewith it should be understood that any suitable suction tube design may be utilized with the current invention. For example, in one embodiment the tube may have a circular, square, or triangular geometry that is either fixed or variable along its length.

Figure 3:
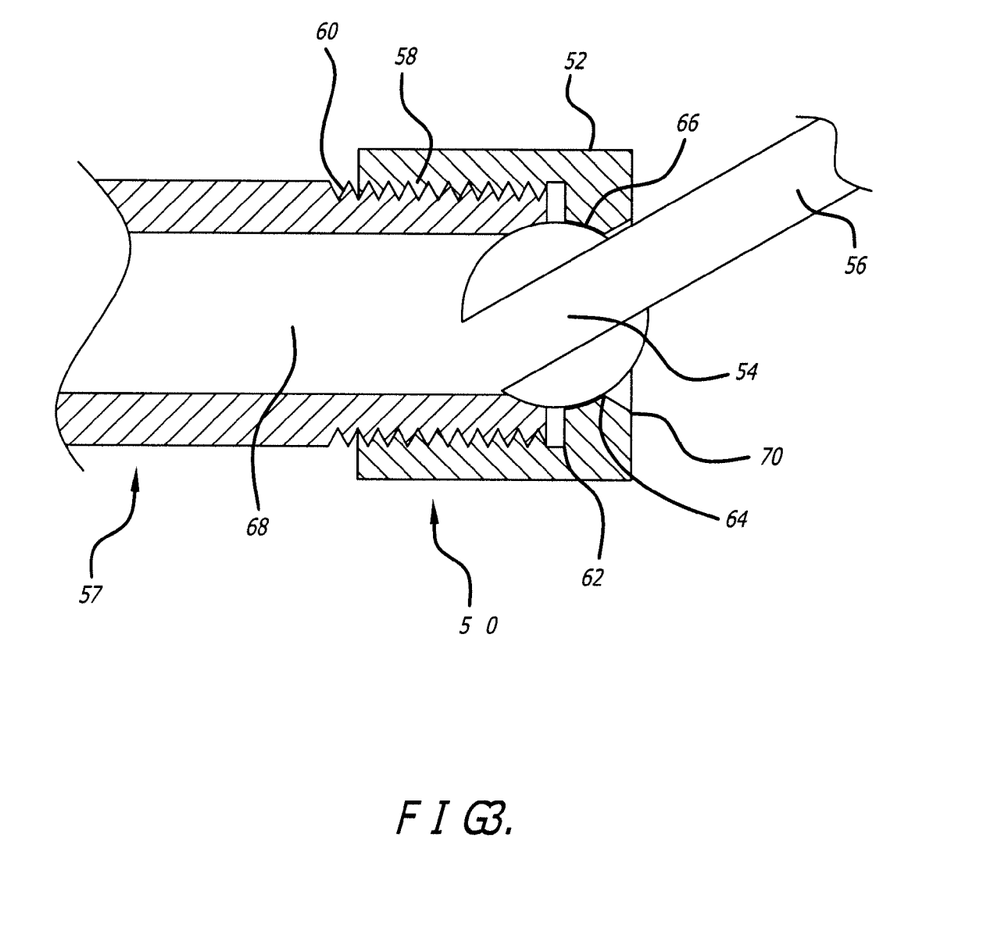
FIG. 3 is a cross-sectional view of one embodiment of the handle/shaft connection of the nerve root retractor and sucker in conjunction with the present invention.

Moreover, although a single retractor/sucker shaft being permanently affixed to the handle is shown in the embodiment pictured in FIGS. 1a and 1b, it should be understood that a detachable shaft may be used in the current invention. One exemplary embodiment of a suitable detachable shaft connection is shown in FIG. 3, however, any suitable fixed geometry or variable geometry attachment may be used in the current invention. For example, the shaft may be attached through a threaded connection, a snap-fit connection, or a friction connection. In such an embodiment, the apparatus may include multiple shafts having variable lengths and/or geometries such that the user can change the instrument to suit any instantaneous need during an operation.

Figure 1G:
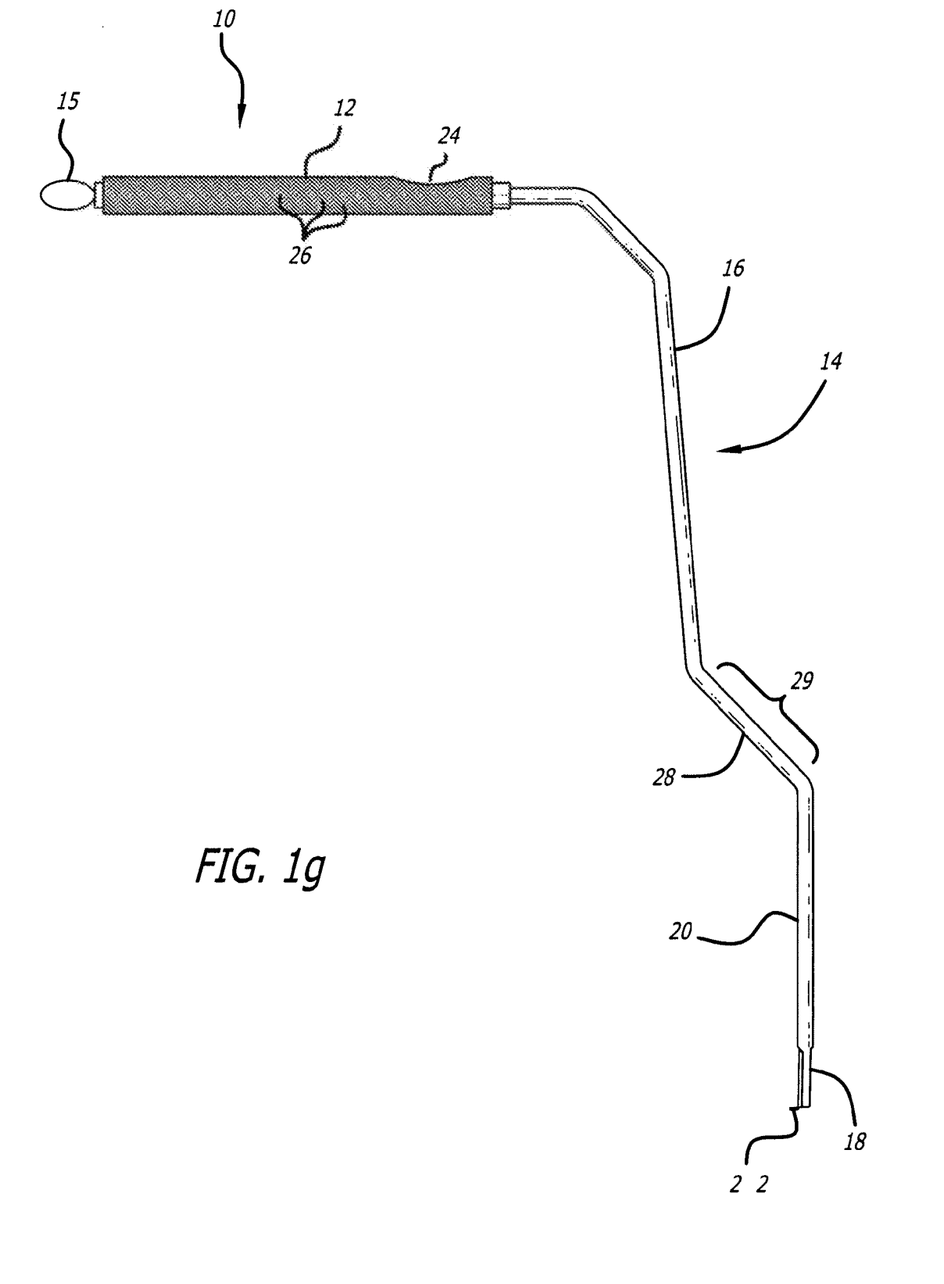
FIG. 1g is a side view of an embodiment of a low profile nerve root retractor and sucker in accordance with the present invention.

In addition, although a conventional shaft design is discussed above, the shaft may be provided in a bayonet or other low profile design for use where visualization of the surgical area is required, such as when a microscope technique is used. One exemplary embodiment of such a bayonet or "offset" nerve root retractor and sucker is shown in FIG. 1g. As shown, in this embodiment the shaft 14 is bent at a nearly 90 degree angle from the handle 12. In addition, the tip portion 20 of the shaft 14 has a further bend section 28 to provide the user better visualization of the retractor 22 and, in turn, the retracted nerve when using a microscope. Although any suitable offset distance 29 may be utilized, in one embodiment the offset is about 1.5 to 1.75 inches.

Although only fixed geometry nerve root retractor and suckers are discussed above, one variable geometry embodiment of the nerve root retractor and sucker according to the present invention is shown in FIGS. 2a to 2f. As shown, in this variable geometry embodiment, like in the fixed geometry apparatus discussed above, the nerve root retractor and sucker 30 generally comprises a handle portion 32 having a nerve root retractor/sucker shaft 34 attached at one end thereof and having a suction connection 35 at the opposite end thereof. Moreover, the design of the nerve root retractor/sucker shaft including the hollow suction tube 36, the suction opening 38, and the retractor 42 are also identical to those discussed above in relation to FIGS. 1a and 1b. In addition, the handle 32 of the embodiment shown in FIGS. 2a and 2b, like those shown in FIGS. 1a and 1b, is hollow such that it may provide a fluid connection between the suction source (not shown) attached at the suction connection 35 and the suction tube 36. A suction control vent 44 is also bored into the handle of the apparatus to provide the user a manual means for reducing the suction provided to the tip of the apparatus during operation, and any number and size of suction vents could be provided such that variable control of the intensity of the suction provided at the tip of the device may be provided.

Figure 2A:
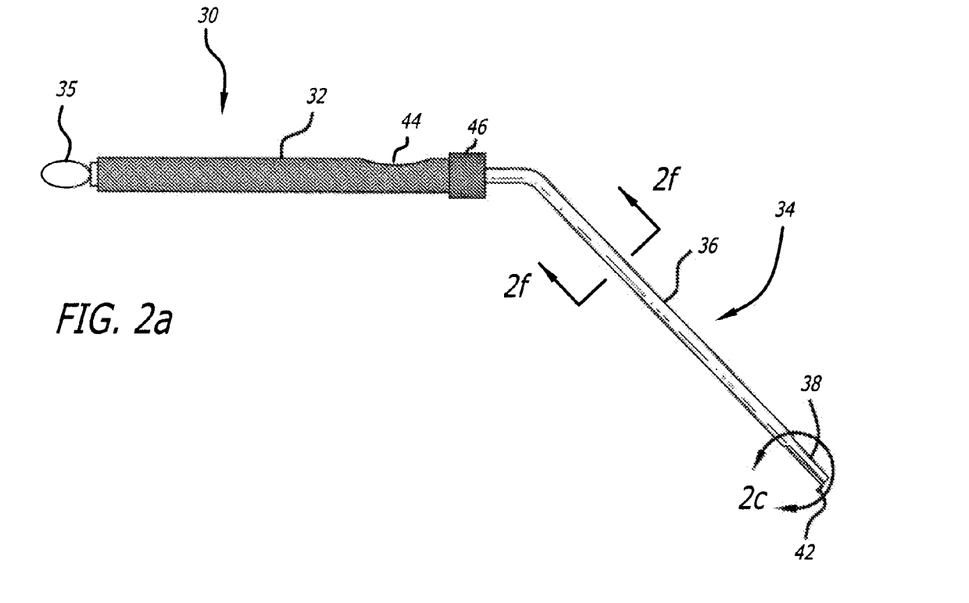
FIG. 2a is a side view of a second embodiment of a nerve root retractor and sucker in accordance with the present invention.
Figure 2B:
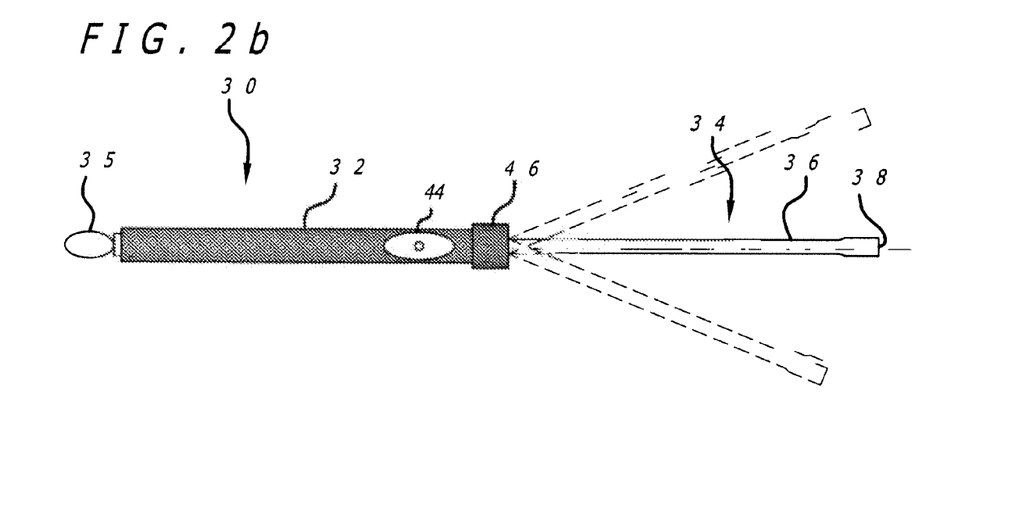
FIG. 2b is a top view of a second embodiment of a nerve root retractor and sucker in accordance with the present invention.
Figure 2C:
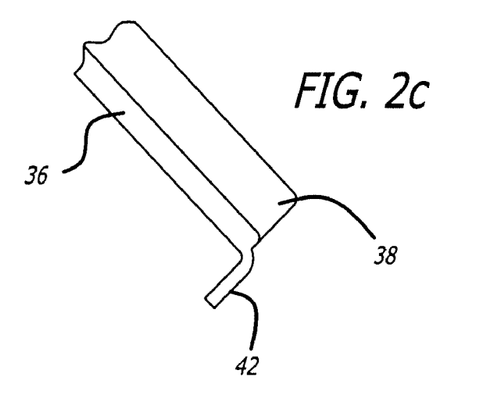
FIG. 2c is a detailed view, "view-A" identified in FIG. 2a, of a second embodiment of a nerve root retractor and sucker in accordance with the present invention.
Figure 2D:
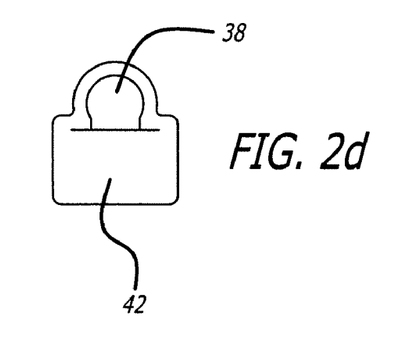
FIG. 2d is a cross-section taken along line "A-A" of FIG. 2a of a second embodiment of a nerve root retractor and sucker in accordance with the present invention.
Figure 2E:
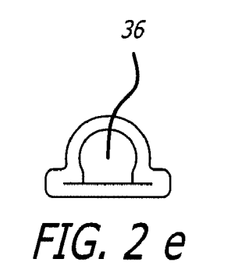
FIG. 2e is a cross-section taken along line "B-B" of FIG. 2a of a second embodiment of a nerve root retractor and sucker in accordance with the present invention.
Figure 2F:
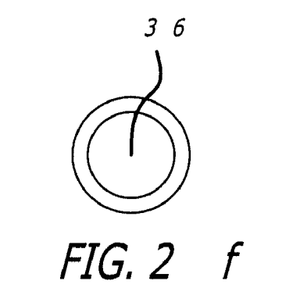
FIG. 2f is a cross-section taken along line "C-C" of FIG. 2a of a second embodiment of a nerve root retractor and sucker in accordance with the present invention.

However, in contrast to the fixed geometry device, in the embodiment shown in FIGS. 2a and 2b, the connection 46 between the handle 32 and the shaft 34 is designed to allow the movement of the shaft relative to the handle in at least one axis. As shown in FIGS. 2a and 2b, preferably the connection is designed to provide polyaxial movement to the shaft.

One embodiment of a connector 50 suitable for providing polyaxial movement to a nerve root retractor/sucker shaft in accordance with the current invention is shown in FIG. 3. As shown, the connector 50 generally comprises a cap 52 against which a connection end of the nerve root retractor/sucker shaft 54 is retained and through which a suction end of the nerve root retractor/sucker shaft 56 extends, and which is designed to threadingly mate with a connector end of the handle 57 and thereby secure the shaft therein.

Specifically, the connector 50 comprises a cap body 52 having an inner threading 58, which is intended to mate with the threading 60 on the connection end 57 of handle. A central annular opening 62 is provided in the center of the connector 50 defining a passage 64 passing therethrough, the passage 64 and opening 62 being designed such that the suction end of the shaft 56 can fit therethrough, but through which the connection end of the shaft 54 cannot fit, such that when the connector 50 is connected to the connection end of the handle 57 the shaft is retained, as shown in FIG. 3.

In such an embodiment, as shown, the connection end of the shaft 54 may be designed in a ball and socket arrangement, with an expanded spherical portion 66 which allows polyaxial motion of the shaft, and which is also dimensioned to prevent the connection end of the shaft from slipping out of the opening 62. In turn, to prevent the shaft from slipping down into the internal passage 68 of the handle, the connection end of the shaft should be dimensioned such that the diameter of the spherical portion 66 is greater than the diameter of the internal passage 68 of the handle. In such an embodiment, tightening the connector cap 52 onto the connection end of the handle 57 presses the spherical portion 66 of the shaft 54 against the opening of the handle 57 which serves to both attach the shaft 54 onto the handle and simultaneously prevent further polyaxial motion of the shaft, thereby fixing the angular position of shaft in relation to the handle. In addition, it should be understood that where suction is directed through the handle to the distal end of the shaft that the connection between the shaft and handle must be designed to be substantially air tight to prevent leakage and a reduction in the strength of suction at the connection joint. For example, either of the spherical portion of the shaft or the connector may be may of a semi-resilient material such that an air tight seal is formed therebetween when tightened.

Although one embodiment of the connector is shown in FIG. 3, it should be understood that alternative designs that allow some continuous or graduate axial movement of the shaft in relation to the handle may be utilize. For example, the cap may take any suitable for, such as an externally threaded cap to provide a low profile device, or a cap having an entirely different connection scheme such as a snap on cap or a frictionally connected cap. Moreover, as shown, the opening 62 may have angled edges 70 to provide greater angular movement to the shaft. It should be understood that while an angular opening of about 60 degrees is shown in this embodiment, any angle suitable for retaining the shaft therein may be used. In addition, although a spherical shaft connection is shown in this embodiment, any suitable connection end that allows the retention of the shaft within the cap while simultaneously providing some motion to the shaft can be utilized. For example, the shaft connection may be hinged, or may include a partial or semicircular shaft end to provide movement of the shaft in at least one axis.

In addition, although FIGS. 2a and 2b show a device with a range of movement along the vertical and horizontal axis of about 60 degrees, it should be understood that any suitable range of movement could be provided. For example, notches could be etched into the side of the connection shown to provide greater than 90 degrees of movement to the shaft.

Regardless of the particular mechanical design used for the apparatus of the current invention it should be understood that any biologically suitable material may be used in the current invention, such as metals, alloys, plastics, ceramics, etc. In one embodiment both the handle and shaft are constructed of one material. Alternatively, the handle and shaft may be made of different materials. In one such embodiment, the shaft is made at least partially of a malleable material, such as a precious metal alloy, or a plastic that would allow a user to deform the shaft into a desired shape during operation.

The invention is also directed to a nerve root retractor and sucker system including a single handle as described above, in combination with a plurality of detachable nerve root retractor/sucker shafts. In this embodiment a variety of different shaped, sized, or constructed shafts could be provided such that the user could change the geometry of the nerve root retractor and sucker to conform with the changing conditions of the surgical opening.

Finally, the invention is also directed to a method of using a nerve root retractor and sucker as described above in a spinal surgery procedure. In this embodiment the nerve root retractor and sucker would be utilized after opening the patient to clear the surgical opening of fluids and debris using the sucker, while preventing damage to the nerve by retracting it from the area of interest.

Although specific embodiments are disclosed herein, it is expected that persons skilled in the art can and will design alternative nerve root retractor and sucker devices, systems, and methods of using such devices and systems that are within the scope of the following claims either literally or under the Doctrine of Equivalents.

What is claimed is:

1. A nerve root retractor and sucker comprising:
   a handle having proximal and distal ends,
   a nerve root retractor/sucker shaft having a proximal open end and a distal open end and defining a central passage therebetween, wherein the proximal end of the shaft is connected to the distal end of the handle, and wherein the angle between the shaft and the axis of the handle may be controllably and fixedly varied along at least one axis;
   a suction source in fluid communication with the distal opening of the shaft, wherein one or both of the handle and shaft define a suction fluid path between the suction source and the distal opening;

at least one suction control vent disposed along the suction fluid path such that closing the at least one vent increases the level of suction at the distal opening, and such that opening the at least one vent decreases the level of suction at the distal opening; and a retractor blade disposed immediately proximate to the distal end of the shaft.

2. The nerve root retractor and sucker described in claim 1, wherein the angle of the shaft to the handle may be varied polyaxially.

3. The nerve root retractor and sucker described in claim 1, wherein the angle of the shaft may be varied in at least a 60 degree arc.

4. The nerve root retractor and sucker described in claim 1, wherein the shaft is connected to the handle in a lockable ball and socket arrangement.

5. The nerve root retractor and sucker described in claim 1, wherein the connection between the shaft and handle forms an airtight connection.

6. The nerve root retractor and sucker described in claim 1, wherein the shaft is detachably connected to the handle.

7. The nerve root retractor and sucker described in claim 1, wherein the handle has distal and proximal openings and defines a hollow passage therebetween, and wherein the proximal opening is in fluid communication with the suction source and the distal opening is in fluid communication with the proximal opening of the shaft.

8. The nerve root retractor and sucker described in claim 7, wherein the at least one suction control vent is disposed on the handle.

9. The nerve root retractor and sucker described in claim 1, having at least two suction control vents.

10. The nerve root retractor and sucker described in claim 9, wherein the at least two suction control vents have different diameters.

11. The nerve root retractor and sucker described in claim 1, wherein the shaft is made of a material selected from the group consisting of stainless steel, plastic, and titanium.

12. The nerve root retractor and sucker described in claim 1, wherein the shaft is made of a material that is malleable at room temperature.

13. The nerve root retractor and sucker described in claim 1, wherein the shaft has a length between about 80 and about 220 mm.

14. The nerve root retractor and sucker described in claim 1, wherein the retractor blade has a width of about 5 to about 10 mm.

15. The nerve root retractor and sucker described in claim 1, wherein the distal end of the shaft forms about a 135 degree angle with the proximal end of the shaft.

16. The nerve root retractor and sucker described in claim 1, wherein the handle includes a non-slip surface.

17. The nerve root retractor and sucker described in claim 1, wherein the retractor blade is detachably connected to the shaft.

18. The nerve root retractor and sucker described in claim 1, wherein the retractor blade is made of a malleable material.

19. The nerve root retractor and sucker described in claim 1, wherein at least one of the length and width of the retractor blade is variable.

20. The nerve root retractor and sucker described in claim 1, wherein the shaft is a compound shape comprising a first straight portion interconnected between the distal end of the handle and the proximal end of a second straight portion through two angled regions such that the axis of the two straight portions are parallel, wherein the axes of the two straight portions form angles of less than 180 degrees with the axis of the handle.

21. A nerve root retractor and sucker system comprising:

a handle having proximal and distal ends, a plurality of nerve root retractor/sucker shafts each having a proximal open end and a distal open end and defining a central passage therebetween, wherein the proximal end of each shaft may be detachably connected to the distal end of the handle, and wherein the axis along the distal end of each of the shafts and has a length of between about 80 and 220 mm, and wherein the angle between the shaft and the axis of the handle may be controllably and fixedly varied along at least one axis;

a suction source in fluid communication with the distal opening of the attached shaft, wherein one or both of the handle and shaft define a suction fluid path between the suction source and the distal opening;

at least one suction control vent disposed along the suction fluid path such that closing the at least one vent increases the level of suction at the distal opening, and such that opening the at least one vent decreases the level of suction at the distal opening; and a retractor blade disposed immediately proximate to the distal end of each of the plurality of shafts, wherein the length of at least two of the plurality of shafts are different.

22. The nerve root retractor and sucker described in claim 21, wherein at least one of the length and width of the retractor blade of at least two of the plurality of shafts are different.

23. The nerve root retractor and sucker described in claim 21, wherein at least one of the shafts is a compound shape comprising a first straight portion interconnected between the distal end of the handle and the proximal end of a second straight portion through two angled regions such that the axis of the two straight portions are parallel, wherein the axes of the two straight portions form angles of less than 180 degrees with the axis of the handle.

* * * * *